United States Patent [19]

Jungbauer et al.

[11] Patent Number: 5,447,656

[45] Date of Patent: Sep. 5, 1995

[54] META-SUBSTITUTED AROMATIC COMPOUNDS HAVING SIX-MEMBERED RINGS, FOR USE IN LIQUID-CRYSTAL MIXTURES

[75] Inventors: Dietmar Jungbauer, Darmstadt; Hubert Schlosser, Glashütten/Ts., both of Germany

[73] Assignee: Hoechst Aktiengesellschaft, Frankfurt, Germany

[21] Appl. No.: 88,849

[22] Filed: Jul. 7, 1993

[30] Foreign Application Priority Data

Jul. 9, 1992 [DE] Germany .................. 42 22 565.5

[51] Int. Cl.$^6$ .................. C09K 19/52; C09K 19/34; G02F 1/13; C07D 239/02; C07C 43/00
[52] U.S. Cl. .................. 252/299.01; 252/299.61; 252/299.62; 252/299.63; 252/299.64; 252/299.65; 252/299.66; 252/299.67; 359/104; 544/298; 544/335; 544/336; 568/585; 568/592
[58] Field of Search .................. 252/299.01, 299.61, 252/299.62, 299.63, 299.64, 299.65, 299.66, 299.67; 359/103, 104; 544/3, 298, 335, 336, 358; 548/136, 146; 549/356, 369, 377, 429, 512; 560/55, 56; 568/585, 592

[56] References Cited

U.S. PATENT DOCUMENTS

| | | | |
|---|---|---|---|
| 3,600,445 | 8/1971 | Wirth et al. | 568/633 |
| 4,943,384 | 7/1990 | Sucrow et al. | 252/299.61 |
| 5,015,797 | 5/1991 | Lee et al. | 585/467 |
| 5,047,170 | 9/1991 | Huynh-ba et al. | 252/299.6 |

FOREIGN PATENT DOCUMENTS

| | | |
|---|---|---|
| 1488494 | 6/1967 | France . |
| 62-126102 | 6/1987 | Japan . |
| 2255635 | 10/1990 | Japan . |
| WO86/05484 | 9/1986 | WIPO . |

*Primary Examiner*—Shean Wu
*Attorney, Agent, or Firm*—Curtis, Morris & Safford

[57] ABSTRACT

Meta-substituted aromatic compounds having six-membered rings, for use in liquid-crystal mixtures Compounds of the formula I $$R^1(-A^1)_a(-M^1)_b(-A^2)_c(-M^2)_d(-A^3)_e(-M^3)_f-\underset{(X^4)=(X^3)}{\overset{(X^1)-\underset{}{\overset{R^2}{\diagup}}}{\diagdown}}(X^2),\quad (I)$$

in which
X is CH, CF or N,
R$^2$ is, for example, an alkyl, ether or ester group, which may also contain a chiral center, and
R$^1$(—A$^1$)$_a$(—M$^1$)$_b$(—A$^2$)$_c$(—M$^2$) $_d$(—A$_3$)$_e$(—M$_3$)$_f$ is a mesogenic radical, can advantageously be used as components of liquid-crystal mixtures, in particular ferroelectric liquid-crystal mixtures.

The substances of the formula I have a particularly favorable effect on the optical switching angle and the critical pulse area of the mixtures.

11 Claims, No Drawings

META-SUBSTITUTED AROMATIC COMPOUNDS HAVING SIX-MEMBERED RINGS, FOR USE IN LIQUID-CRYSTAL MIXTURES

BACKGROUND OF THE INVENTION

Particularly in the last decade, liquid crystals have been introduced into various industrial areas in which electro-optical and display-device properties are required (for example in watch, calculator and typewriter displays). These display devices are based on dielectric alignment effects in the nematic, cholesteric and smectic phases of the liquid-crystalline compounds, where—caused by the dielectric anisotropy—the molecular long axis of the compounds adopts a preferential alignment in an applied electric field. The usual response times in these display devices are too long for many other potential areas of application of liquid crystals. This disadvantage is particularly noticeable if a large number of pixels must be addressed. Production costs of equipment containing relatively large screen areas are then generally too high.

In addition to nematic and cholesteric liquid crystals, optically active smectic liquid crystals have also been increasing in importance for the last few years.

Clark and Lagerwall have shown that the use of ferroelectric liquid crystals (FLCs) in very thin cells results in electro-optical switching or display elements which have response times faster by a factor of 1,000 compared with conventional TN ("twisted nematic") cells (cf., for example, Lagerwall et al., "Ferroelectric Liquid Crystals for Displays", SID Symposium, October Meeting 1985, San Diego, Calif., USA). On the basis of this and other favorable properties, for example the possibility of bistable switching and the virtually viewing angle-independent contrast, FLCs are in principle highly suitable for the abovementioned areas of application, for example via matrix addressing. Ferroelectric liquid crystals are also particularly suitable in the area of spatial light modulators (cf., for example, U. Elton in "Spatial Light Modulators and Applications", SPIE, Vol. 1150, pp. 46 ff) due to their high contrast and fast response speed. However, the response speed of ferroelectric liquid-crystal mixtures is generally still not sufficient to drive, for example, high-resolution, fast display elements. It is therefore desirable to find components which increase the response speed of liquid-crystalline mixtures.

The molecular structure of the liquid crystals which can be employed for the abovementioned areas of application is essentially based on para- or 1,4-substituted aromatic and saturated six-membered rings, such as 1,4-phenylene, pyridine-2,5-diyl, pyrimidine-2,5-diyl and trans-1,4-cyclohexylene, which, through linking to one another, either directly or via suitable intermediate pieces, and by linking to suitable terminal groups give the elongate rod-shaped molecules known from numerous examples (see, for example, in: D. Demus, H. Zaschke, "Flüssige Kristalle in Tabellen I und II" [Liquid Crystals in Tables I and II], VEB Deutscher Verlag für Grundstoffindustrie, Leipzig 1974 and 1984).

By contrast, liquid-crystalline compounds which contain, as substructure, an exclusively meta- or 1,3-substituted six-membered aromatic ring have hitherto not been described, since it was expected that the use of such a unit would disturb the rod-shaped molecule geometry and would thus not give any liquid-crystalline properties.

SUMMARY OF THE INVENTION

Surprisingly, it has now been found that meta-substituted aromatic compounds having six-membered rings, of the formula (I), also form liquid-crystalline phases and, in addition, can advantageously be employed in liquid-crystal mixtures.

The present invention therefore relates to compounds of the formula (I)

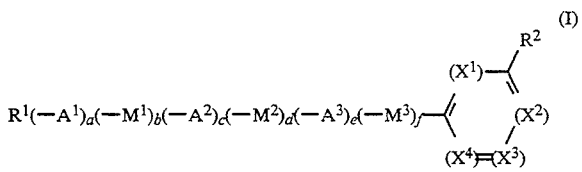

in which the symbols and indices have the following meanings:

$R^1$ and $R^2$ independently of one another, are a straight-chain or branched alkyl radical having 1 to 22 carbon atoms (with or without asymmetrical carbon atoms), it also being possible for one or two —$CH_2$— groups to be replaced by —O—, —S—, —CO—, —CO—O—, —O—CO—, —CO—S—, —S—CO—, —O—CO—O—, —CH=CH—, —C≡C—, cyclopropanediyl or —Si($CH_3$)$_2$—, and it also being possible for one or more hydrogen atoms in the alkyl radical to be substituted by F, Cl, Br or CN, or are one of the following chiral groups:

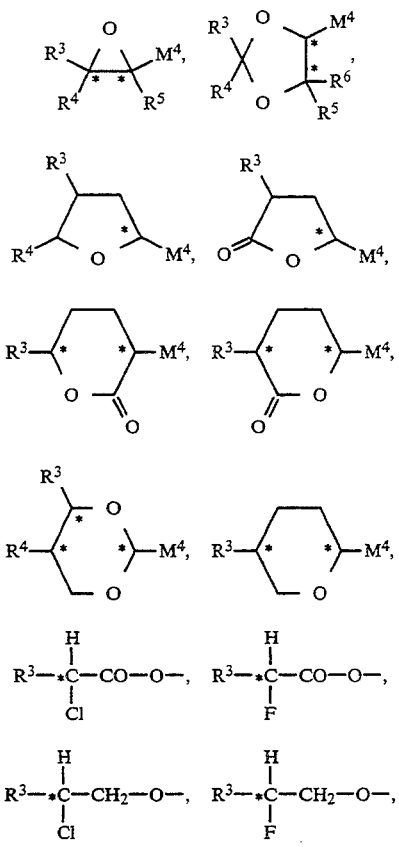

-continued

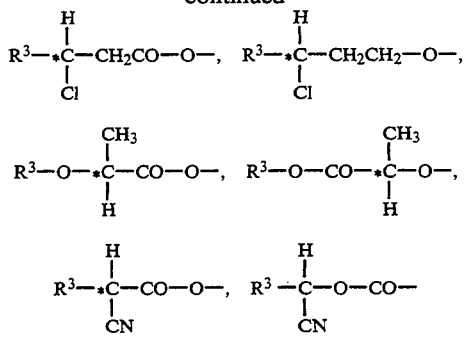

DESCRIPTION OF THE PREFERRED EMBODIMENTS $R^1$ and $R^2$ are preferably, independently of one another, a straight-chain or branched alkyl radical having 1 to 15 carbon atoms (with or without asymmetrical carbon atoms), it also being possible for one or two non-adjacent —CH$_2$— groups to be replaced by —O—, —S—, —CO—, —CO—O—, —O—CO—, —O—CO—O—, —CH=CH—, —C≡C—, cyclopropanediyl or —Si(CH$_3$)$_2$—, or are one of the following chiral groups:

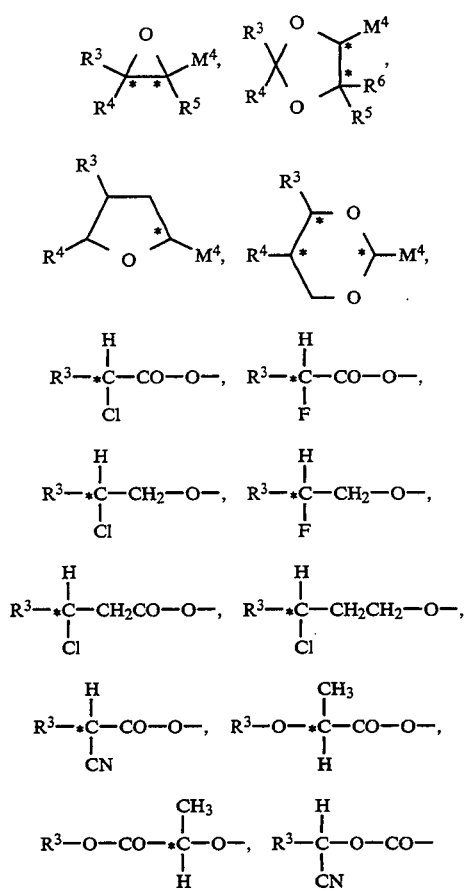

$R^1$ and $R^2$ are particularly preferably, independently of one another, a straight-chain or branched alkyl radical having 1 to 10 carbon atoms (with or without asymmetrical carbon atoms), it also being possible for one or two —CH$_2$— groups to be replaced by —O—, —CO—, —CO—O—, —O—CO—, —CH=CH—, —C≡C—, cyclopropanediyl or —Si(CH$_3$)$_2$—, or are one of the following chiral groups:

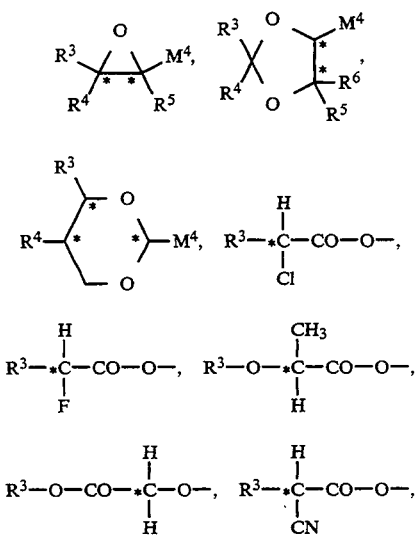

$R^1$ and $R^2$ are especially preferably, independently of one another, an alkyl radical having 1 to 8 carbon atoms, it also being possible for one or two —CH$_2$— groups to be replaced by —O—, —OCO— or cyclopropanediyl, or are the chiral groups:

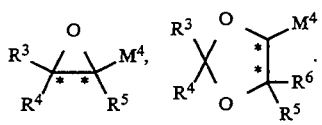

$R^3$, $R^4$, $R^5$ and $R^6$ independently of one another, are B or a straight-chain or branched alkyl radical having 1 to 22 carbon atoms, it also being possible for one or two —CH$_2$ groups to be replaced by —O—, —S—, —CO—, —CO—O—, —O—CO—, —CO—S—, —S—CO—, —O—CO—O—, —CH=CH—, —C≡C—, cyclopropanediyl or —Si(CH$_3$)$_2$—, or $R^3$ and $R^4$ together may alternatively be —(CH$_2$)$_4$— or —(CH$_2$)$_5$— if they are bonded as substituents to a dioxolane system.

$R^3$, $R^4$, $R^5$ and $R^6$ are preferably, independently of one another, H or a straight-chain or branched alkyl radical having 1 to 15 carbon atoms, it also being possible for one or two —CH$_2$— groups to be replaced by —O—, —S—, —CO—, —CO—O—, —O—CO—, —CO—S—, —S—CO—, —O—CO—O—, —CH=CH—, —C≡C—, cyclopropanediyl or —Si(CH$_3$)$_2$—, or $R^3$ and $R^4$ together may alternatively be —(CH$_2$)$_4$— or —(CH$_2$)$_5$— if they are bonded as substituents to a dioxolane system.

$R^3$, $R^4$, $R^5$ and $R^6$ are particularly preferably, independently of one another, H or a straight-chain or branched alkyl radical having 1 to 10 carbon atoms, it also being possible for one or two —CH$_2$— groups to be replaced by —O—, —S—, —CO—, —CO—O—, —O—CO—, —CO—S—, —S—CO—, —O—CO—O—, —CH=CH—, —C≡C—, cyclopropanediyl or —Si(CH$_3$)$_2$—, or $R^3$ and $R^4$ together may alternatively be —(CH$_2$)$_4$— or —(CH$_2$)$_5$— if they are bonded as substituents to a dioxolane system.

$R^3$, $R^4$, $R^5$ and $R^6$ are in particular, independently of one another, H or a straight-chain or branched alkyl radical having 1 to 8 carbon atoms.

$A^1$, $A^2$ and $A^3$, independently of one another, are 1,4-phenylene, in which one or two hydrogen atoms may be replaced by F, Cl and/or CN, pyrazine-2,5-diyl, pyridazine-3,6-diyl, pyridine-2,5-diyl, pyrimidine-2,5-diyl, in which one or two hydrogen atoms may be replaced by F, trans-1,4-cyclohexylene, in which one or two hydrogen atoms may be replaced by —CN and/or —CH$_3$, 1,3,4-thiadiazole-2,5-diyl, 1,3-dioxane-2,5-diyl, 1,3-dithiane-2,5-diyl, 1,3-thiazole-2,4-diyl, 1,3-thiazole-2,5-diyl, thiophene-2,4-diyl, thiophene-2,5-diyl, piperazine-1,4-diyl, piperazine-2,5-diyl, naphthalene-2,6-diyl, bicyclo[2.2.2]octane-1,4-diyl, 1,3-dioxaborinane-2,5-diyl or trans-decalin-2,6-diyl.

$A^1$ may alternatively be a group of the formula

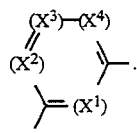

$A^1$, $A^2$ and $A^3$ are preferably, independently of one another, 1,4-phenylene, pyrazine-2,5-diyl, pyridazine-3,6-diyl, pyridine-2,5-diyl, pyrimidine-2,5-diyl, in which one or two hydrogen atoms may be replaced by F, trans-1,4-cyclohexylene, 1,3,4-thiadiazole-2,5-diyl, 1,3-dioxane-2,5-diyl, naphthalene-2,6-diyl or bicyclo-2.2.2]octane-1,4-diyl.

$A^3$ may alternatively be a group of the formula

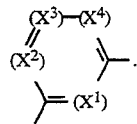

$A^1$, $A^2$ and $A^3$ are particularly preferably, independently of one another, 1,4-phenylene, pyrazine-2,5-diyl, pyridine-2,5-diyl, pyrimidine-2,5-diyl, in which one or two hydrogen atoms may be replaced by F, trans-1,4-cyclohexylene, 1,3,4-thiadiazole-2,5-diyl., naphthalene-2,6-diyl or 1,3-dioxane-2,5-diyl.

$A^1$ may alternatively be a group of the formula

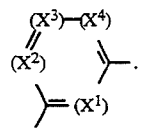

$A^1$, $A^2$ and $A^3$ are especially preferably, independently of one another, 1,4-phenylene, pyridine-2,5-diyl, pyrimidine-2,5-diyl, in which one or two hydrogen atoms may be replaced by F, or trans- 1,4-cyclohexylene.

$A^1$ may alternatively be a group of the formula

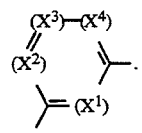

$M^1$, $M^2$ and $M^3$ independently of one another, are —O—, —S—, —CO—, —CO—O—, —O—CO—, —CO—S—, —S—CO—, —O—CO—O—, —CH$_2$—O—, —O —CH$_2$—, —CH$_2$CH$_2$—, —CH=CH— or —C≡C—.

$M^1$, $M^2$ and $M^3$ are preferably, independently of one another, —O—, —CO—, —CO—O—, —O—CO—, —CH$_2$—O—, —O—CH$_2$—, —CH$_2$CH$_2$—, —CH=CH— or —C≡C—.

$M^1$, $M^2$ and $M^3$ are particularly preferably, independently of one another, —O—, —CO—O—, —O—CO—, —CH$_2$—O—, —O—CH$_2$—, —CH$_2$CH$_2$—, —CH=C— or —C≡C—.

$M^1$, $M^2$ and $M^3$ are especially preferably, independently of one another, —O—, —CO—O—, —O—CO—, —O—CH$_2$—, —CH$_2$—O— or —CH$_2$CH$_2$—.

$M^4$ is —CH$_2$—O—, —O—CH$_2$—, —CO—O—, —O—CO— or a single bond.

$X^1$, $X^2$, $X^3$ and $X^4$ are CH, CF or N, where the number of nitrogen atoms is 0, 1 or 2.

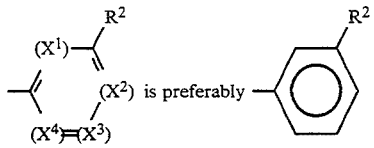

a, b, c, d, e and f are zero or one, with the proviso that the total a+c+e is 1, 2 or 3.

* is a center of chirality.

The compounds according to the invention are prepared by methods known per se from the literature, as described in standard works on organic synthesis, for example Houben-Weyl, Methoden der Organischen Chemie [Methods of Organic Chemistry], Georg-Thieme-Verlag, Stuttgart.

The preparation is carried out under reaction conditions which are known and suitable for said reactions. Use may also be made here of variants which are known per se, but are not described here in greater detail. As far as the synthesis of the radical "RAMAMAM" is concerned, reference is made, for example, to DE-A 23 44 732, 24 50 088, 24 29 093, 25 02 904, 26 36 684, 27 01 591 and 27 52 975 for compounds containing 1,4-cyclohexylene and 1,4-phenylene groups; German Patent 26 41 724 for compounds containing pyrimidine-2,5-diyl groups; DE-A 40 26 223 and EP-A 0 391 203 for compounds containing pyridine-2,5-diyl groups; DE-A 32 31 462 for compounds containing pyridazine-3,6-diyl groups; DE-A 29 44 905 and 32 27 916 for compounds containing 1,3-dioxane-2,5-diyl groups; DD 160 061 for compounds containing 1,3-dithiane-2,5-diyl groups; U.S. Pat. Nos. 4,261,652 and 4,219,256 for compounds containing 1,4-bicyclo[2.2.2]octane-1,4-diyl groups; N. Miyaura, T. Yanagi and A. Suzuki in Synthetic Communications 11 (1981), pp. 513–519, for the direct linking of aromatic rings and heteroaromatic rings; DE-A 32 01 721 for compounds containing —CH$_2$CH$_2$— bridges, and Koji Seto et al. in Liquid Crystals 8 (1990), pp. 861–870, for compounds containing —C≡C— bridges.

Strategies for the synthesis of 1,3-disubstituted benzenes are found, for example, in J. March, Advanced Organic Chemistry, McGraw-Hill Kogaskusha Ltd.

The preparation of 2,4-, 2,6- and 3,5-disubstituted pyridines, 2,6-disubstituted pyrazines, 2,4- and 4,6-disubstituted pyrimidines and 3,5-disubstituted pyridazines is given, for example, in the appropriate volumes of the series "The Chemistry of Heterocyclic Compounds" by A. Weissberger and E. C. Taylor (editors).

If desired, the starting materials can also be formed in situ by not isolating them from the reaction mixture, but instead immediately converting them further into the compounds of the formula (I).

The compounds of the formula (I) according to the invention are suitable as components for use in liquid-crystal mixtures, in particular in ferroelectric liquid-crystal mixtures, where the compounds of the formula (I) need not necessarily themselves be liquid-crystalline. The LC mixtures may contain from 0.01 to 60% by weight, preferably from 0.1 to 40% by weight, particularly preferably from 0.1 to 20% by weight, of one or more of the compounds of the formula (I). The other constituents are preferably selected from known compounds having nematic, cholesteric and/or smectic phases; these include, for example, Schiff bases, biphenyls, terphenyls, phenylcyclohexanes, cyclohexylbiphenyls, N—, S— and O-containing heterocyclic compounds, for example pyrimidines, cinnamic esters, cholesterol esters or various bridged, polycyclic esters of p-alkylbenzoic acids with terminal polar groups. Such mixtures preferably contain from 2 to 20 components.

The compounds according to the invention can also be employed in nematic liquid-crystal mixtures.

Surprisingly, it has now been found that addition of compounds of the formula (I) can improve the optical switching angle and considerably reduce the critical pulse area (CPA) on electro-optical switching of these liquid-crystal mixtures.

In addition, the compounds of the formula I have a broad range of applications. Depending on the choice of substituents, these compounds can be used as base materials from which liquid-crystalline, smectic, in particular ferroelectric, phases are predominantly composed; however, compounds of the formula (I) can also be added to liquid-crystalline base materials from other classes of compound in order, for example, to vary the dielectric and/or optical anisotropy and/or the viscosity and/or the spontaneous polarization and/or the phase ranges and/or the tilt angle and/or the pitch of a dielectric of this type.

The mixtures according to the invention can in turn be used in electro-optical or fully optical elements, for example display elements, switching elements, light modulators, elements for image processing and/or signal processing or generally in the area of non-linear optics.

The invention is described in greater detail by means of the examples below.

EXAMPLES

For the ferroelectric liquid-crystal mixtures, the values for the spontaneous polarisation $P_a[nC/cm^2]$ are measured by the method of H. Diamant et al. (Rev. Sci. Instr., 28, 30, 1957) in measurement cells with an electrode separation of 10 $\mu$m without an alignment layer at a temperature of 25° C.

The critical pulse area (CPA) is defined as follows: a rectangular electric pulse of suitable voltage (polarity) and duration can, for a given cell thickness, convert one stable switching state permanently into another if the voltage and/or pulse duration are sufficiently high. The CPA is obtained from the product of a pulse duration of 50 $\mu$sec, the minimum voltage necessary for fully permanent switching and the reciprocal of the cell density (T=25° C.).

The switching angle $2\Theta_{eff}$ is determined at 25° C. from the difference in angles of the two previous switching states after short-circuiting the electrodes. The measurements of the CPA and $2\Theta_{eff}$ are carried out using glass test cells approximately 1.8 $\mu$m thick with ITO electrodes and a rubbed polyvinyl alcohol (PVA) alignment layer. The filled cells are switched for 1 minute at 25° C. by means of rectangular pulses ($IOH_2$) in a 15 V/$\mu$m electric field before the actual measurements are carried out.

The phase-conversion temperatures are determined from the changes in texture during heating and cooling with the aid of a polarizing microscope. By contrast, the melting point is determined by means of a DSC instrument. The phase-conversion temperatures between the phases

| Isotropic | (I) |
|---|---|
| Nematic | (N or N*) |
| Smectic A | ($S_A$) |
| Smectic C | ($S_C$ or $S_C$*) |
| Crystalline | (X) | are given in ° C., and the values are between the phase designations in the phase sequence. The first data given are the phase transitions on heating into the isotropic phase, followed by the phase transitions during cooling, if they differ significantly from those during heating.

EXAMPLE 1

2-(3-Methoxyphenyl)-5-(4-octyloxyphenyl), pyrimidine:

25.43 g (0.64 mol) of a 60% strength by weight sodium hydride dispersion in mineral oil are added in portions at room temperature to 100 g (0.58 mol) of commercially available 3-bromophenol in 600 ml of dimethylformamide, the mixture is stirred for a further half an hour, and 66.5 ml (0.58 mol) of commercially available benzyl chloride are added dropwise. The mixture is stirred at room temperature for 1 hour, 1 l of water is added, and the solid which precipitates is filtered off, washed with water and recrystallized from 600 ml of isopropanol, giving 108 g of 3-benzyloxybromobenzene.

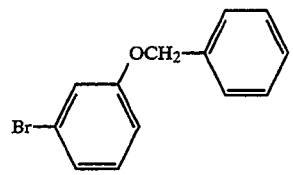

62 g (0.236 mol) of 3-benzyloxybromobenzene, 6.64 g (0.277 mol) of magnesium and 0.3 g of iodine are reacted in 800 ml of tetrahydrofuran at 60° C. for 2 hours to give the solution of the corresponding Grignard compound, which is subsequently added dropwise to a solution, cooled to 0° C. of 28.77 g (0.277 mol) of trimethyl borate in 300 ml of tetrahydrofuran. The mixture is stirred at 0° C. for 1 hour, 74 ml of 37% strength hydrochloric acid in 300 ml of water are added, and the reaction mixture is subsequently partitioned between water and ether. The organic phase is washed twice with water, dried over sodium sulfate, evaporated and recrystallized from hexane, giving 33.65 g of 3-benzyloxybenzeneboronic acid.

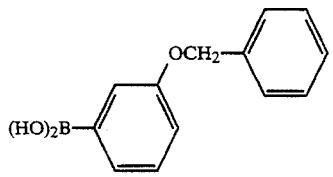

15.00 g (63.10 mmol) of 2,5-dibromopyrimidine (for preparation see: D. W. Arantz and D. J. Brown in Journal of the Chemical Society C, 1971, p. 1889), 14.40 g (63.10 mmol) of 3-benzyloxybenzeneboronic acid, 13.40 g (126.2 mmol) of sodium carbonate and 0.73 g (0.63 mmol) of tetrakis(triphenylphosphine)palladium(0) are heated at 80° C. for 4 hours in 150 ml of toluene, 75 ml of ethanol and 50 ml of water. The reaction mixture is subsequently partitioned between ether and water, the organic phase is washed twice with sodium chloride solution, dried over sodium sulfate and evaporated, and the residue is purified by chromatography (silica gel/dichloromethane), giving 15.14 g of 5-bromo-2-(3-benzyloxyphenyl)pyrimidine.

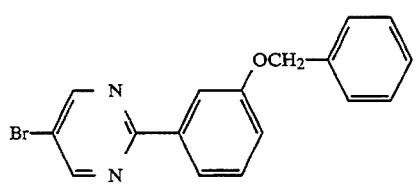

8.00 g (23.40 mmol) of 5-bromo-2-(3-benzyloxyphenyl)pyrimidine, 7.03 g (28.10 mmol) of 4-octyloxybenzeneboronic acid (preparation analogous to 3-benzyloxybenzeneboronic acid), 7.00 g (65.52 mmol) of sodiumcarbonate and 0.27 g (0.23 mmol) of tetrakis(triphenylphosphine)palladium(0) are heated at 80° C. for 2 hours in 200 ml of toluene, 100 ml of ethanol and 50 ml of water. The reaction mixture is subsequently partitioned between water and ether, the organic phase is washed twice with sodium chloride solution, dried over sodium sulfate and evaporated, and the residue is purified by chromatography (silica gel/dichloromethane: ethyl acetate=98:2), giving 10.66 g of 2-(3-benzyloxyphenyl)-5-(4-octyloxyphenyl)pyrimidine.

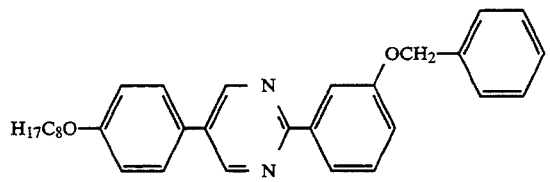

10.66 g (22.84 mmol) of 2-(3-benzyloxyphenyl)-5-(4-octyloxyphenyl)pyrimidine are hydrogenated together with 2.00 g of Pd (10%)/C in 100 ml of tetrahydrofuran until the calculated volume of hydrogen has been consumed, the catalyst is subsequently filtered off, and the filtrate is evaporated and dried, giving 8.43 g of 2-(3-hydroxyphenyl)-5-(4-octyloxyphenyl)pyrimidine.

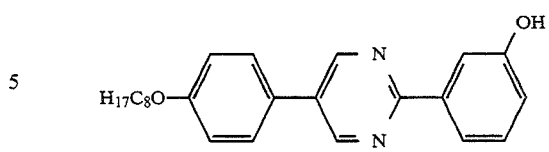

1.50 g (5.76 mmol) of triphenylphosphine and 0.90 ml (5.76 mmol) of diethyl azodicarboxylste in 40 ml of tetrahydrofuran are stirred at 0° C. for 30 minutes. 1.50 g (3.84 mmol) of 2-(3-hydroxyphenyl)-5-(4-octyloxyphenyl)pyrimidine and 0.23 ml (5.76 mmol) of methanol are subsequently added, and the resultant solution is stirred at room temperature overnight. Evaporation to dryness, chromatographic purification (silica gel/dichloromethane:ethyl acetate=95:5) and recrystallization from acetonitrile give 1.20 g of 2-(3-methoxyphenyl)-5-(4-octyloxyphenyl)pyrimidine.

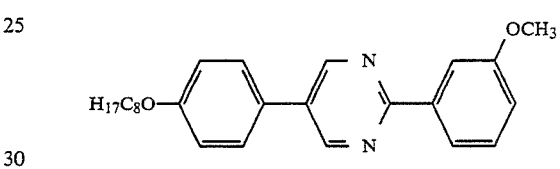

The compound has the phase sequence:
X 70 $S_A$ 98 I 98 $S_A$ 37 X

The substance is denoted by $S_1$ below.

EXAMPLE 2

2-(3-Ethoxyphenyl)-5-(4-octyloxyphenyl)pyrimidine:

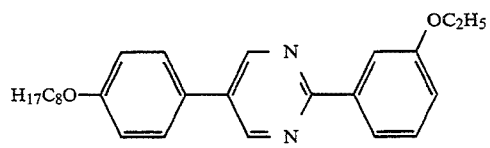

The synthesis is carried out analogously to Example 1. The compound has the phase sequence:
X 83 I 71 $S_c$ 60 X The substance is denoted by $S_2$ below.

EXAMPLE 3

5-(4-Octyloxyphenyl)-2-(3-propoxyphenyl)pyrimidine:

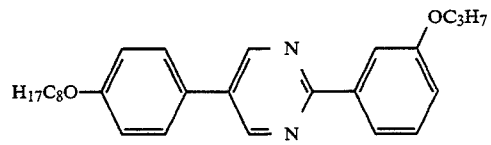

The synthesis is carried out analogously to Example 1. The compound has the phase sequence:
X 84 I 76 $S_A$ 61 $S_c$ 50 X The substance is denoted by $S_3$ below.

EXAMPLE 4

5-(4-Hexyloxyphenyl)-2-(3-propoxyphenyl)pyrimidine:

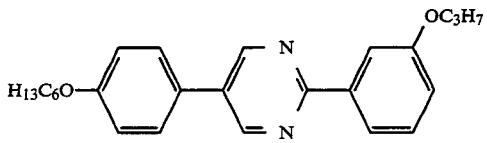

The synthesis is carried out analogously to Example 1.
The compound has the phase sequence:
X 83 I 71.5 S$_A$ 49 X

EXAMPLE 5

5-(4-Butoxyphenyl)-2-(3-propoxyphenyl)pyrimidine:

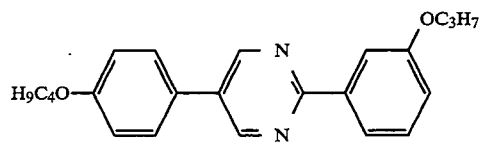

The synthesis is carried out analogously to Example 1.
The compound has the phase sequence:
X 95 I 95 S$_x$ 57 X

EXAMPLE 6

2-(3-Hexyloxyphenyl)-5-(4-hexyloxyphenyl)pyrimidine:

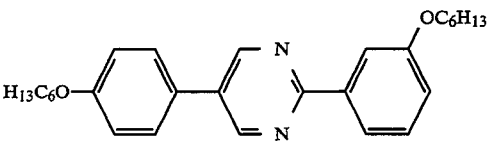

The synthesis is carried out analogously to Example 1.
The compound has the phase sequence:
X 87 S$_x$ 88 I 75 S$_x$ 59 X

EXAMPLE 7

5-(4-Butoxyphenyl)-2-(3-hexyloxyphenyl)pyrimidine:

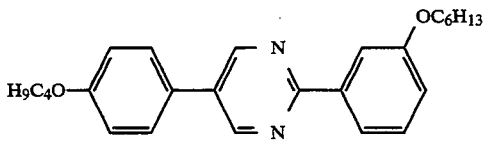

The synthesis is carried out analogously to Example 1.
The compound has the phase sequence:
X 86 I 75 S$_x$ 65 X

EXAMPLE 8

5-(4-Decyloxyphenyl)-2-(3-propoxyphenyl)pyrimidine:

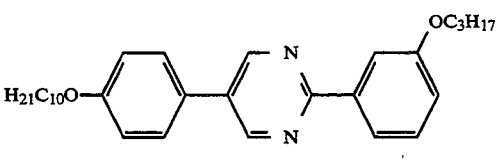

The synthesis is carried out analogously to Example 1.
The compound has the phase sequence:
X 78.4 I 76 S$_A$ 60 S$_c$ 41.5 X

EXAMPLE 9

2-(3-Cyclopropylmethoxyphenyl)-5-(4-octyloxyphenyl)pyrimidine:

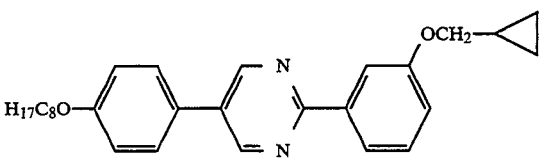

The synthesis is carried out analogously to Example 1.
The compound has the phase sequence:
X 98.1 I 58.6 X

EXAMPLE 10

2,5-Bis (3-propoxyphenyl)pyrimidine:

3-Bromophenol and 1-bromopropane are reacted analogously to Example 1 to give 3-propoxybromobenzene.

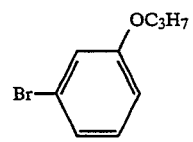

3-Propoxybromobenzene is converted analogously to Example 1 into 3-propoxybenzeneboronic acid.

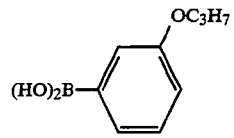

2.0 g (8.4 mmol) of 2,5-dibromopyrimidine, 4.54 g (25.2 mmol) of 3-propoxybenzeneboronic acid, 5.34 g (50.4 mmol) of sodium carbonate and 0.10 g (0.9 mmol) of tetrakis(triphenylphosphine)palladium(0) are heated at 80° C. for 6 hours in 50 ml of toluene, 25 ml of ethanol and 25 ml of water. The reaction mixture is subsequently partitioned between water and ether, the organic phase is washed twice with sodium chloride solution, dried over sodium sulfate and evaporated, and the residue is purified by chromatography (silica gel/dichloromethane:ethyl acetate=98:2) and by recrystallization from n-hexane, giving 1.31 g of 2,5-bis(3-propoxyphenyl)pyrimidine.

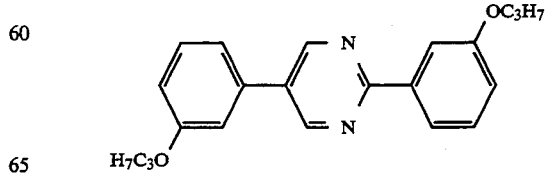

The compound has the phase sequence:
X 81 I 31.6 X

EXAMPLE 11

2-(3-Methoxyphenyl)-5-octyloxypyrimidine:

A solution of 4.76 g (85.3 mmol) of potassium hydroxide in 20 ml of ethylene glycol is added dropwise over the course of 2 hours at 180° C. to 7.26 g (21.3 mmol) of 2-(3-benzyloxyphenyl)-5-bromopyrimidine and 0.035 g (1.08 mmol) of sulfur in 60 ml of ethylene glycol. The mixture is kept at 180° C. for a further 3 hours, poured into water and acidified by means of 37% strength hydrochloric acid, and the solid which precipitates is isolated by filtration. Purification by chromatography (silica gel/hexane: ethyl acetate=32) gives 4.77 g of 2-(3-benzyloxyphenyl)-5-hydroxypyrimidine.

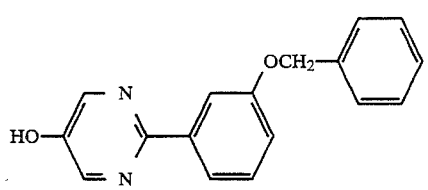

5.52 g (21.05 mmol) of triphenylphosphine and 3.67 g (21.05 mmol) of diethyl azodicarboxylate are stirred at 0° C. for 30 minutes in 100 ml of tetrahydrofuran. 3.90 g (14.03 mmol) of 2-(3-benzyloxyphenyl)-5-hydroxypyrimidine and 2.74 g (21.05 mmol) of 1-octanol are subsequently added, and the resultant solution is stirred at room temperature for 18 hours. Evaporation to dryness and purification by chromatography (silica gel/dichloromethane) give 4.25 g of 2-(3-benzyloxyphenyl)-5-octyloxypyrimidine.

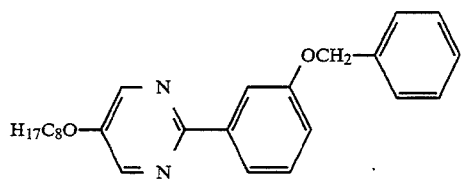

Removal of the benzyl protecting group by hydrogenation analogously to Example 1 gives 2-(3-hydroxyphenyl)-5-octyloxypyrimidine.

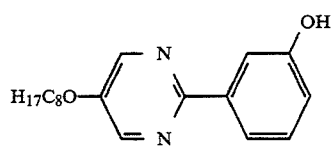

2-(3-Hydroxyphenyl)-5-octyloxypyrimidine is reacted with methanol analogously to Example 1 to give 2-(3-methoxyphenyl)-5-octyloxypyrimidine.

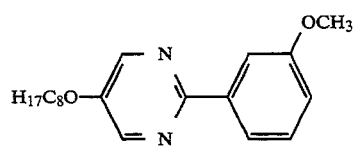

The compound has the phase sequence:
X43 I

EXAMPLE 12

2-(3-Ethoxyphenyl)-5-octyloxypyrimidine:

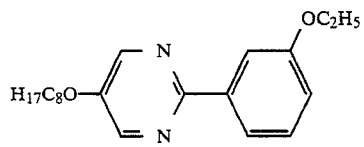

The synthesis is carried out analogously to Example 11. The compound has the phase sequence:
X50 I

EXAMPLE 13

5-Octyloxy-2-(3-propoxyphenyl)pyrimidine:

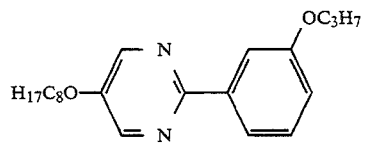

The synthesis is carried out analogously to Example 11. The compound has the phase sequence:
X56 I

EXAMPLE 14

5-(3-Methoxyphenyl)-2-(4-octyloxyphenyl)pyrimidine:

2,5-Dibromopyrimidine and 4-octyloxybenzeneboronic acid are reacted analogously to Example 1 to give 5-bromo-2-(4-octyloxyphenyl) pyrimidine.

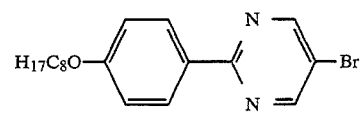

5-Bromo-2-(4-octyloxyphenyl)pyrimidine and 3-benzyloxybenzeneboronic acid are reacted analogously to Example 1 to give 5-(3-benzyloxyphenyl)-2-(4-octyloxyphenyl)pyrimidine.

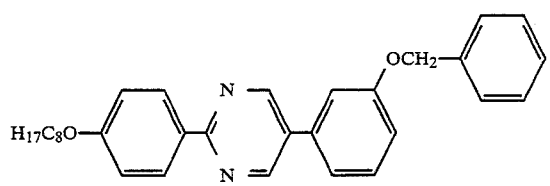

Removal of the benzyl protecting group from 5-(3-benzyloxyphenyl)-2-(4-octyloxyphenyl) pyrimidine by hydrogenation analogously to Example i gives 5-(3-hydroxyphenyl)-2-(4-octyloxyphenyl) pyrimidine.

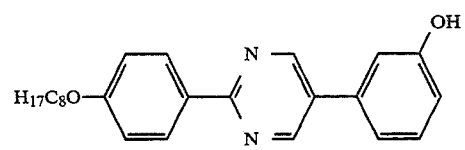

5-(3-Hydroxyphenyl)-2-(4-octyloxyphenyl)pyrimidine is reacted with methanol analogously to Example 1 to give 5-(3-methoxyphenyl)-2-(4-octyloxyphenyl)-pyrimidine.

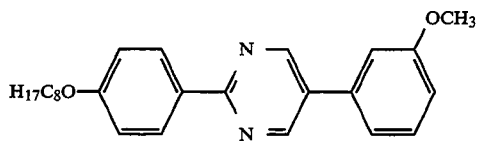

The compound has the phase sequence:
X 98 I

EXAMPLE 15

5-(3-Ethoxyphenyl)-2-(4-octyloxyphenyl)pyrimidine:

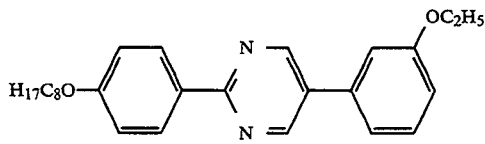

The synthesis is carried out analogously to Example 14. The compound has the phase sequence:
X 108 I

EXAMPLE 16

2-(4-Octyloxyphenyl)-5-(3-propoxyphenyl)pyrimidine:

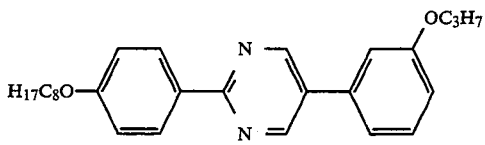

The synthesis is carried out analogously to Example 14. The compound has the phase sequence:
X 107 I

EXAMPLE 17

5-[4-((2S,3S)-3-Butyloxiran-2-ylmethoxy)phenyl]-2-(3-propoxyphenyl)pyrimidine:

2,5-Dibromopyrimidine and 3-propoxybenzeneboronic acid are reacted analogously to Example 1 to give 5-bromo-2-(3-propoxyphenyl) pyrimidine.

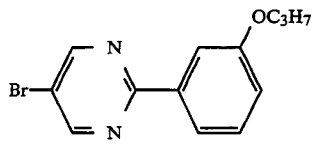

5-Bromo-2-(3-propoxyphenyl)pyrimidine and 4-benzyloxybenzeneboronic acid (preparation analogous to 3-benzyloxybenzeneboronic acid) are reacted analogously to Example 1 to give 5-(4-benzyloxyphenyl)-2-(3-propoxyphenyl)pyrimidine.

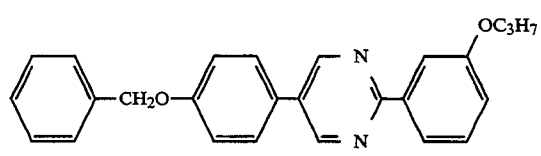

Removal of the benzyl protecting group from the above compound by hydrogenation analogously to Example 1 gives 5-(4-hydroxyphenyl)-2-(3-propoxyphenyl)pyrimidine.

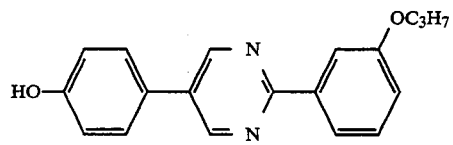

5-(4-Hydroxyphenyl)-2-(3-propoxyphenyl)pyrimidine and (2S,3S)-3-butyloxiran-2-ylmethanol(preparation described in EP-0 046 033 and Journal of the American Chemical Society, Volume 109, 1987, page 5765) are reacted analogously to Example 1 to give 5-[4-((2S,3S)-3-butyloxiran-2-ylmethoxy)phenyl]-2-(3-propoxyphenyl)pyrimidine.

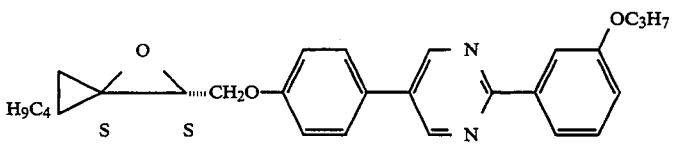

$[\alpha]_D^{20}$ (CHCl₃) = −17.25
The compound has the phase sequence:
X 89.7 I 84 $S_A$ 53 $S_Z$ 49.8 X

EXAMPLE 18

5-[3-((2S,3S)-3-Butyloxiran-2-ylmethoxy)phenyl]-2-(4-octyloxyphenyl)pyrimidine:

The synthesis is carried out analogously to Example 1 from 5-(3-hydroxyphenyl)-2-(4-octyloxyphenyl)pyrimidine and (2S, 3S)-3-butyloxiran-2-ylmethanol.

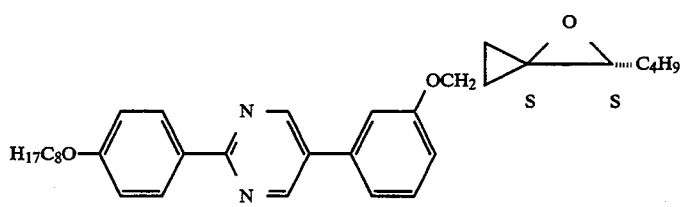

$[\alpha]_D^{20}$ (CHCl₃) = −14.27

The compound has the phase sequence:
X 91 I

EXAMPLE 19

2-[3-((2S,3S)-3-Butyloxiran-2-ylmethoxy)phenyl]-5-octyloxypyrimidine:

The synthesis is carried out analogously to Example 11 from 2-(3-hydroxyphenyl)-5-octyloxypyrimidine and (2S,3S)-3-butyloxiran-2-ylmethanol.

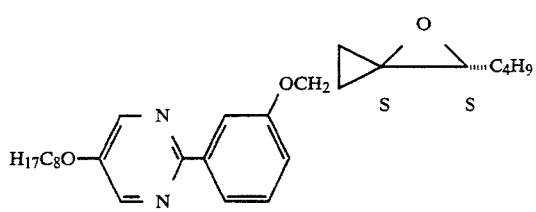

$[\alpha]_D^{20}$ (CHCl₃) = −14.74

The compound has the phase sequence:
X 48 I

EXAMPLE 20

5-[4-((4S)-2,2-Dimethyl-1,3-dioxolan-4-ylmethoxy)-phenyl]-2-(3-propoxyphenyl)pyrimidine:

The synthesis is carried out analogously to Example 17 from 5-(4-hydroxyphenyl)-2-(3-propoxyphenyl)-pyrimidine and (4S)-2,2-dimethyl-1,3-dioxolan-4-ylmethanol (commercially available).

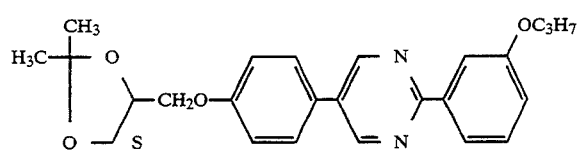

$[\alpha]_D^{20}$ (CHCl₃) = +5.0

The compound has the phase sequence:
X 107.1 I 85.0 X

EXAMPLE 21

4-[2-(3-propoxyphenyl)pyrimidin-5-yl]phenyl (2R,3R)-3-propyloxirane-2-carboxylate:

1.5 g (4.90 mmol) of 5-(4-hydroxyphenyl)-2-(3-propoxyphenyl)pyrimidine, 1.12 g (7.4 mmol) of sodium (2R,3R)-3-propyloxirane-2-carboxylate (prepared as described in DE 43 04 756), 2.80 g (7.4 mmol) of hydroxybenzotriazoletetramethyluronium hexafluorophosphate and 0.81 ml (7.4 mmol) of N-methylmorpholine are stirred at room temperature for 17 hours in 40 ml of acetonitrile with exclusion of light. For work-up, the reaction mixture is partitioned between dichloromethane and aqueous sodium hydrogencarbonate solution, and the organic phase is washed with aqueous sodium chloride solution, dried over magnesium sulfate, filtered and evaporated. Purification by chromatography (silica gel/dichloromethane: ethyl acetate=20:1) and recrystallization from acetonitrile give 0.9 g of product.

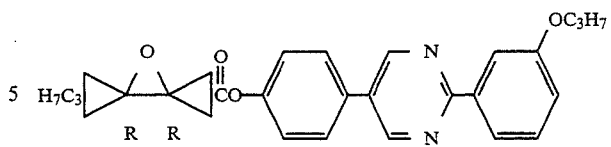

$[\alpha]_D^{20}$ (CHCl₃) = −13.0

The compound has the phase sequence:
X 116 I 82 X

EXAMPLE 22

3-[5-(4-octyloxyphenyl)pyrimidin-2-yl]phenyl(2R,3R)-3-propyloxirane-2-carboxylate:

The synthesis is carried out analogously to Example 21.

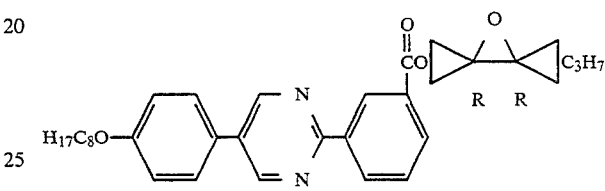

$[\alpha]_D^{20}$ (CHCl₃) = +0.33

The compound has the phase sequence:
X 111 I

EXAMPLE 23

4-[2-(3-Propoxyphenyl)pyrimidin-5-yl]phenyl(4S)-2,2-di-methyl-1,3-dioxolane-4-carboxylate:

The synthesis is carried out analogously to Example 21 using sodium (4S)-2,2-dimethyl-1,3-dioxolane-4-carboxylate, whose preparation is described in DE 43 04 756.

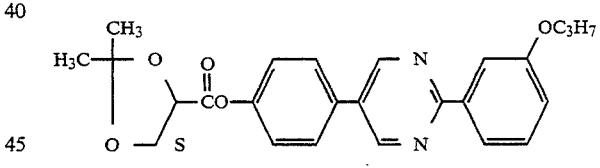

$[\alpha]_D^{20}$ (CHCl₃) = +7.1

The compound has the phase sequence:
X₁ 129 X₂ 136 I 112 X

EXAMPLE 24

3-[5-(4-Octyloxyphenyl)pyrimidin-2-yl]phenyl (4S)-2,2-dimethyl-1,3-dioxolane-4-carboxylate:

The synthesis is carried out analogously to Example 23.

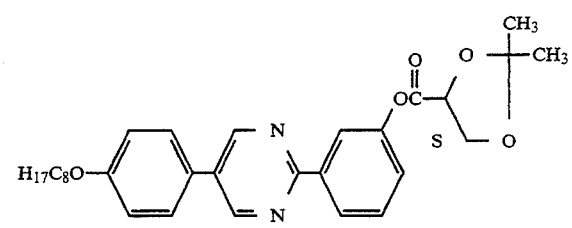

$[\alpha]_D^{20}$ (CHCl₃) = +12.81

The compound has the phase sequence:

EXAMPLE 25

2-(3-Propoxyphenyl)-5-(4-octyloxyphenyl)pyridine:

The synthesis is carried out analogously to Example 1 using commercially available 2,5-dibromopyridine instead of 2,5-dibromopyrimidine.

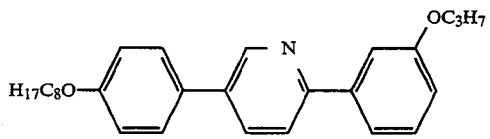

EXAMPLE 26

2-(3-Propoxyphenyl)-5-(4-octyloxyphenyl)pyrazine:

The synthesis is carried out analogously to Example 1 using 2,5-dibromopyrazine ( for preparation see: R. C. Ellingson and R. L. Henry in Journal of the American Chemical Society, Volume 71 (1949), pages 2798 to 2800) instead of 2,5-dibromopyrimidine.

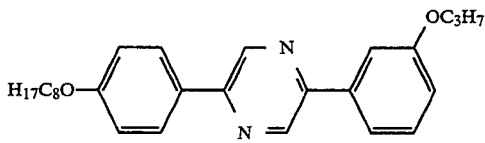

EXAMPLE 27

3-(4-Octyloxyphenyl)-6-(3-propoxyphenyl)pyridazine:

The synthesis is carried out analogously to Example 1 using commercially available 3,6-dichloropyridazine instead of 2,5-dibromopyrimidine.

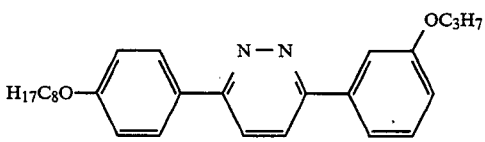

EXAMPLE 28

2-(4-Octyloxyphenyl)-5-(3-propoxyphenyl)thiadiazole:

The synthesis is carried out analogously to the method described by K. Dimitrova, J. Hauschild, H. Zaschke and H. Schubert in Journal für praktische Chemie, Volume 322 (1980), page 933.

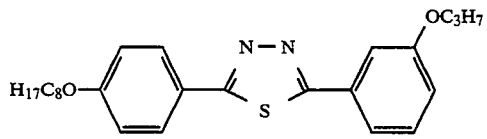

EXAMPLE 29

4-Octyloxy-3'-propoxy[1,1',4',1'']terphenyl:

The synthesis is carried out analogously to Example 1 using commercially available 1,4-dibromobenzene instead of 2,5-dibromopyrimidine.

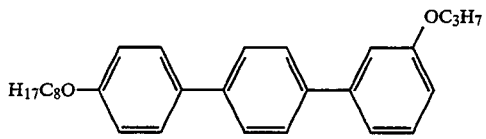

EXAMPLE 30

2',3'-Difluoro-4-octyloxy-3''-propoxy[1,1',4',1'']-terphenyl:

The synthesis is carried out analogously to Example 1 using commercially available 1,4-dibromo-2,3-difluorobenzene instead of 2,5-dibromopyrimidine.

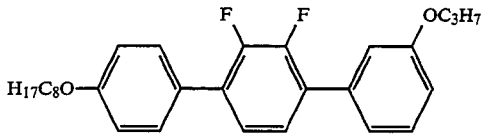

EXAMPLE 31

2-(2-Fluoro-3-propoxyphenyl)-5-(4-octyloxyphenyl)-pyrimidine:

The synthesis is carried out analogously to Example 1 using 3-bromo-2-fluorophenol instead of 3-bromophenol.

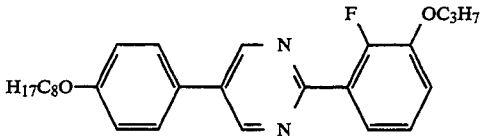

Use Examples 1, 2 and 3

The FLC starting mixture Me employed (containing no substances according to the invention) and having the phase sequence X —4.5 (—10) $S_c{}^*$ 63 $S_A$ 69 $N^*$ 83 I has the following composition (in mol%):

| Structure | mol% |
|---|---|
| $C_8H_{17}$—O—(pyrimidine)—(phenyl)—O—$C_6H_{13}$ | 9.05 |
| $C_8H_{17}$—O—(pyrimidine)—(phenyl)—O—$C_8H_{17}$ | 4.18 |

| Structure | Value |
|---|---|
| 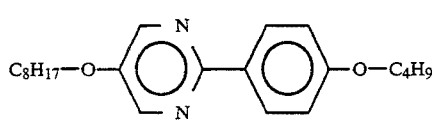 | 9.54 |
| 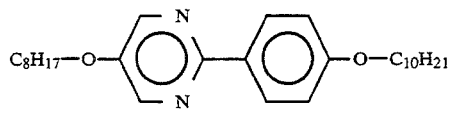 | 7.60 |
| 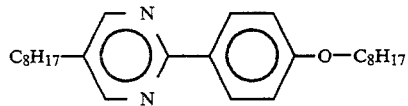 | 13.00 |
| 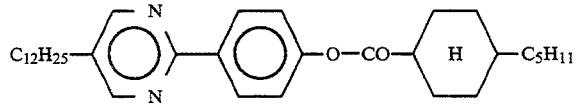 | 14.33 |
| 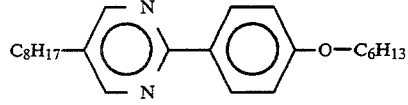 | 14.49 |
| 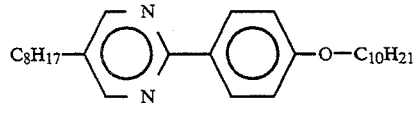 | 9.66 |
| 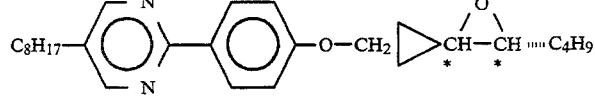 | 10.5 |
| 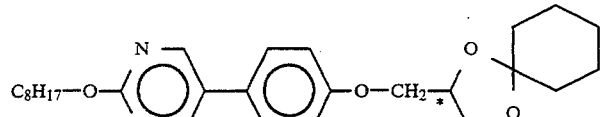 | 1.99 |
| 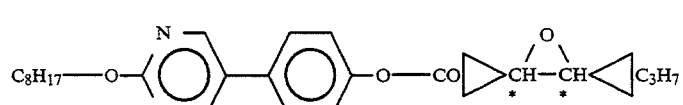 | 5.12 |
| 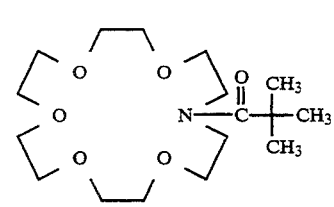 | 0.5 |

The mixtures $M_1$, $M_2$ and $M_3$ employed have the following compositions and the phase sequences stated:

| $M_1$: | 95 mol% $M_0$ + 5 mol% $S_1$ |
|---|---|
|  | $S_C^*$ 60 $S_A$ 74 N* 84 I |
| $M_2$: | 95 mol% $M_0$ + 5 mol% $S_2$ |
|  | $S_C^*$ 59 $S_A$ 74 N* 84 I |
| $M_3$: | 95 mol% $M_0$ + 5 mol% $S_3$ |
|  | X −9 (−17) $S_C^*$ 59 $S_A$ 74 N* 83 I |

It can be seen that addition of substances $S_1$, $S_2$ and $S_3$ slightly increases the N*−I phase transition. This underlines the high suitability of the substances according to the invention as components of liquid-crystal mixtures.

The table below shows the measurement values for $P_s$, $2\Theta_{eff}$ and the CPA at 25° C. of the mixtures $M_0$, $M_1$, $M_2$ and $M_3$.

| Mixture | $P_s \text{nC}^{-1} \text{cm}^2$ | $2\theta_{\mathit{eff}}[°]^{-1}$ | CPA Vs$^{-1}$ m |
|---|---|---|---|
| $M_0$ | 33 | 49 | 900 |
| $M_1$ | 29 | 42 | 730 |
| $M_2$ | 29 | 42 | 630 |
| $M_3$ | 30 | 43 | 710 |

It can be seen how favorably the substances affect the switching angle and CPA. The switching angle is reduced to values only slightly below 45° (physically ideal), which may be regarded as technically excellent. Substances $S_1$ and $S_3$ reduce the CPA by about 20%, substance $S_3$ by as much as 30%. This either has a positive effect on the driver voltage necessary for display—at constant pulse width—or has an advantageous effect on the pulse width for a constant driver voltage.

In addition, it has been found that the substances according to the invention can greatly reduce the melting point.

Use Example 4

5 mol% of the substance according to the invention from Example 9 are added to the FLC starting mixture $M_0$ from Examples 1, 2 and 3. The following phase sequence is determined: X −9 (−16) $S_c$* 57.5 $S_A$ 72.5 N* 82 I. At 25° C., a CPA of 640 Vs/m at a polarization $P_s$ of 40 nC/cm$^2$ and an angle of 45° (ideal value) is measured. The favorable effect on the response speed and angle is again apparent. In addition, the melting point of the mixture is significantly reduced.

Use Example 5

A base mixture

| | % by weight |
|---|---|
| $C_6H_{13}$—O—⟨phenyl⟩—CO—O—⟨phenyl(CH$_3$)⟩—O—CO—⟨phenyl⟩—O—$C_6H_{13}$ | 3.00 |
| $C_6H_{13}$—O—⟨pyrimidine⟩—⟨phenyl⟩—O—$C_6H_{13}$ | 3.48 |
| H—⟨cyclohexyl⟩—⟨phenyl⟩—CO—O—⟨pyrimidine⟩—⟨phenyl⟩—O—$C_8H_{17}$ | 12.69 |
| $C_7H_{15}$—O—⟨pyrimidine⟩—⟨phenyl⟩—O—$C_9H_{19}$ | 6.40 |
| $C_6H_{13}$—O—⟨pyrimidine⟩—⟨phenyl⟩—O—$C_8H_{17}$ | 6.58 |
| $C_8H_{17}$—O—⟨pyrimidine⟩—⟨phenyl⟩—O—$C_6H_{13}$ | 7.24 |
| $C_8H_{17}$—O—⟨pyrimidine⟩—⟨phenyl⟩—O—$C_8H_{17}$ | 7.77 |
| $C_8H_{17}$—O—⟨phenyl⟩—⟨phenyl⟩—O—CO—⟨phenyl⟩—O—$C_4H_8$—Si(CH$_3$)$_2$—$C_4H_9$ | 5.76 |
| $C_8H_{17}$—O—⟨pyridine⟩—⟨pyridine⟩—O—$C_8H_{17}$ | 3.96 |

| | % by weight |
|---|---|
| $C_{10}H_{21}-O-\langle\bigcirc\rangle-CO-O-\langle\bigcirc\rangle-O-C_4H_8-Si(CH_3)_2-C_4H_9$ | 5.29 |
| $C_{10}H_{21}-O-\langle\bigcirc\rangle-C(=N-N=C)-\langle\bigcirc\rangle$ (S bridge) | 6.64 |
| $C_{10}H_{21}-O-\langle\bigcirc\rangle-CO-O-\langle\bigcirc\rangle-O-C_3H_6-CH(CH_3)_2$ rac. | 9.01 |
| $C_8H_{17}-O-\langle\bigcirc\rangle-\langle N\rangle-\langle\bigcirc\rangle-O-C_3H_7$ | 6.30 |
| $C_8H_{17}-O-\langle\bigcirc\rangle-\langle N(F)\rangle-\langle\bigcirc\rangle-O-C_4H_8-Si(CH_3)_2-C_4H_9$ | 8.12 |
| $C_9H_{19}-CO-O-\langle N\rangle-\langle\bigcirc\rangle-O-C_8H_{17}$ | 7.73 | has the phase sequence:
X −21 (−40) $S_c$ 79 $S_A$ 91 N 102 I

10% by weight of the substance from Example 9 are added.

Phase sequence: X −35 (−41) $S_c$ 71 $S_A$ 85 N 98 I
The favorable effect on the melting point is clear.

Use Example 6

The base mixture from Use Example 5 is treated with 10% by weight of the substance from Example 17.

Phase sequence: X −41 (< −45) $S_c$ 66 $S_A$ 96 N 98 I

The good effect on the melting point is again clear here, particularly considering the already very low melting point of the starting mixture.

Use Example 7

The base mixture from Use Example 5 is treated with 5% by weight of the substance from Example 21.

Phase sequence: X 60 (< −45) $S_c^*$ 71 $S_A$ 81 N* 95 I
$P_s(20°\ C.) = 31.1\ nC/cm^2$
$P_s(40°\ C.) = 22.6\ nC/cm^2$
$P_s(60°\ C.) = 13.0\ nC/cm^2$ The very high polarization, even for a small amount of dope, is apparent.

We claim:

1. A liquid-crystal mixture comprising at least one compound of the formula (I)

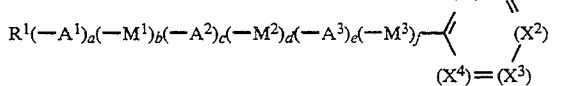

in which the symbols and indices have the following meanings: $R^1$ and $R^2$ independently of one another, are a straight-chain or branched alkyl radical having 1 to 22 carbon atoms (with or without asymmetrical carbon atoms), it also being possible for one or two —$CH_2$— groups to be replaced by —O—, —CO—, —CO—O—, —O—CO—, —O—CO—O—, —CH=CH—, —C≡C—, cyclopropanediyl or —Si($CH_3$)$_2$—, and it also being possible for one or more hydrogen atoms in the alkyl radical to be substituted by F, Cl or CN, or are one of the following chiral groups:

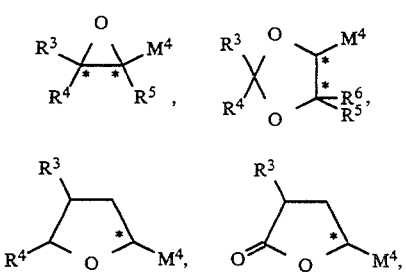

-continued

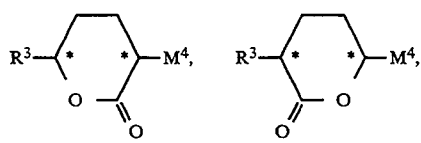

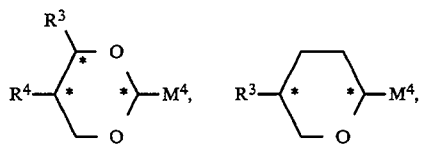

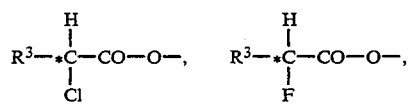

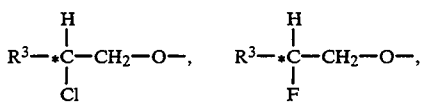

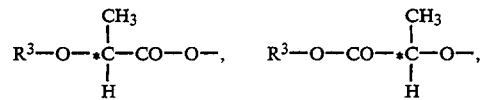

$R^3$, $R^4$, $R^5$ and $R^6$ independently of one another, are H or a straight-chain or branched alkyl radical having 1 to 22 carbon atoms, it also being possible for one or two —CH$_2$— groups to be replaced by —O—, or $R^3$ and $R^4$ together can alternatively be —(CH$_2$)$_4$— or —(CH$_2$)$_5$— if they are bonded as substituents to a dioxolane system;

$A^1$, $A^2$ and $A^3$ independently of one another, are 1,4-phenylene, in which one or two hydrogen atoms can be replaced by F, Cl and/or CN, pyrazine-2,5-diyl, pyridazine-3,6-diyl, pyridine-2,5-diyl, pyrimidine-2,5-diyl, in which one or two hydrogen atoms can be replaced by F, trans-1,4-cyclohexylene, in which one or two hydrogen atoms can be replaced by —CN and/or —CH$_3$, 1,3,4-thiadiazole-2,5-diyl, 1,3-dioxane-2,5-diyl, 1,3-dithiane-2,5-diyl, 1,3-thiazole-2,4-diyl, 1,3-thiazole-2,5-diyl, thiophene-2,4-diyl, thiophene-2,5-diyl, naphthalene-2,6-diyl or transdecalin-2,6-diyl;

$A^1$ can alternatively be a group of the formula

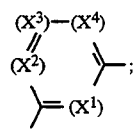

$M^1$, $M^2$ and $M^3$, independently of one another, are —O—, —CO—, $M^4$ is —CH$_2$—O—, —O—CH$_2$—, —CO—O—, —O—CO— or a single bond;

$X^1$, $X^2$, $X^3$ and $X^4$ are CH, CF or N where the number of nitrogen atoms is 0, 1 or 2;

a, b, c, d, e and f are zero or one, with the proviso that the total a+c+e is 1, 2 or 3;

* is a center of chirality; and with the proviso that the group

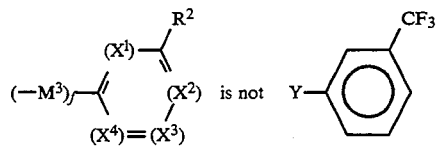

with Y being —CH$_2$—O—, —O—CH$_2$—, —COO—, or —O—CO—.

2. A compound of the formula (I)

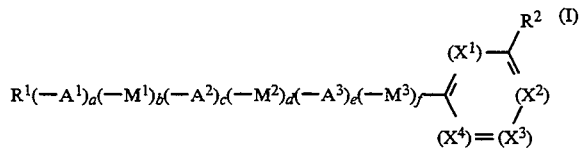

in which the symbols and indices have the following meanings:

$R^1$ is a straight-chain or branched alkyl radical having 1 to 22 carbon atoms (with or without asymmetrical carbon atoms), it also being possible for one or two —CH$_2$— groups to be replaced by —O—, —CO—, —CO—O—, —O—CO—, —O—CO—O—, —CH=CH—, —C≡C—, cyclopropanediyl or —Si(CH$_3$)$_2$—, and it also being possible for one or more hydrogen atoms in the alkyl radical to be substituted by F, Cl or CN;

$R^2$ is a straight-chain or branched alkyl radical having 2 to 22 carbon atoms (with or without asymmetrical carbon atoms), wherein one or two —CH$_2$— groups are replaced by —O—, —CO—, —CO—O—, —O—CO—, —O—CO—O—, —CH=CH—, —C≡C—, cyclopropanediyl or —Si(CH$_3$)$_2$—, and it being possible for one or more hydrogen atoms in the alkyl radical to be substituted by F, Cl or CN, or $R^1$ and $R^2$ independently of one another, are one of the following chiral groups:

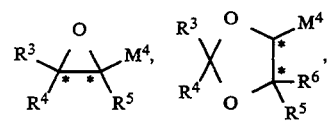

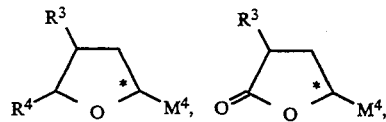

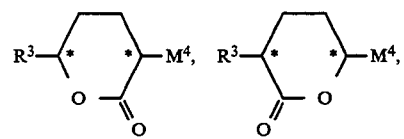

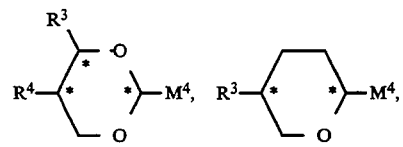

-continued

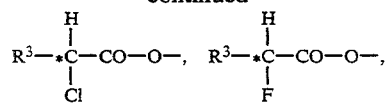

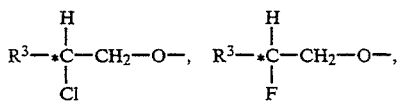

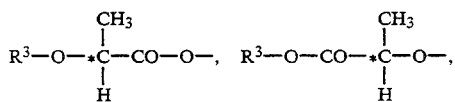

$R^3$, $R^4$, $R^5$ and $R^6$ independently of one another, are H or a straight-chain or branched alkyl radical having 1 to 22 carbon atoms, it also being possible for one or two —$CH_2$— groups to be replaced by —O—, or $R^3$ and $R^4$ together can alternatively be —$(CH_2)_4$— or —$(CH_2)_5$— if they are bonded as substituents to a dioxolane system;

$A^1$, $A^2$ and $A^3$ independently of one another, are 1,4-phenylene, in which one or two hydrogen atoms can be replaced by F, Cl and/or CN, pyrazine-2,5-diyl, pyridazine-3,6-diyl, pyridine-2,5-diyl, pyrimidine-2,5-diyl, in which one or two hydrogen atoms can be replaced by F, trans-1,4-cyclohexylene, in which one or two hydrogen atoms can be replaced by —CN and/or —$CH_3$, 1,3,4-thiadiazole-2,5-diyl, 1,3-dioxane-2,5-diyl, 1,3-dithiane-2,5-diyl, 1,3-thiazole-2,4-diyl, 1,3-thiazole-2,5-diyl, thiophene-2,4-diyl, thiophene-2,5-diyl, naphthalene-2,6-diyl or transdecalin-2,6-diyl;

$A^1$ can alternatively be a group of the formula

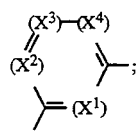

$M^1$, $M^2$ and $M^3$, independently of one another, are —O—, —CO—, —CO—O—, —O—CO—, —O—CO—O—, —$CH_2$—O—, —O—$CH_2$—, —$CH_2CH_2$—, —CH=CH— or —C≡C—;

$M^4$ is —$CH_2$—O—, —O—$CH_2$—, —CO—O—, —O—CO— or a single bond;

$X^1$, $X^2$, $X^3$ and $X^4$ are CH, CF or N, where the number of nitrogen atoms is 0, 1 or 2;

a, b, c, d, e and f are zero or one, with the proviso that the total a+c+e is 1, 2 or 3;

\* is a center of chirality.

3. A compound as claimed in claim 2, the symbols and indices having the following meanings:

$R^1$ is a straight-chain or branched alkyl radical having 1 to 15 carbon atoms (with or without asymmetrical carbon atoms), it also being possible for one or two —$CH_2$— groups to be replaced by —O—, —CO—, —CO—O—, —O—CO—, —O—CO—O—, —CH=CH—, —C≡C—, cyclopropanediyl or —Si$(CH_3)_2$—, and $R^2$ is a straight-chain or branched alkyl radical having 2 to 15 carbon atoms (with or without asymmetrical carbon atoms), wherein one or two —$CH_2$— groups are replaced by —O—, —CO—, —CO—O—, —O—CO—, —O—CO—O—, —CH=CH—, —C≡C—, cyclopropanediyl or —Si$(CH_3)_2$—, or $R^1$ and $R^2$ independently of one another, are one of the following chiral groups:

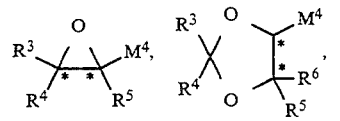

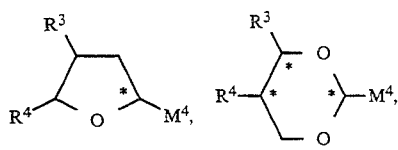

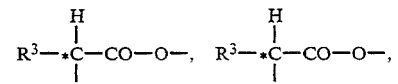

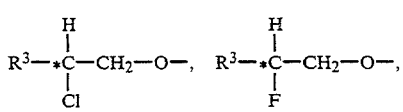

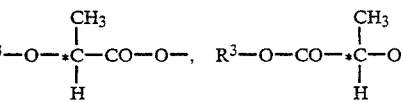

$R^3$, $R^4$, $R^5$ and $R^6$ independently of one another, are H or a straight-chain or branched alkyl radical having 1 to 15 carbon atoms, it also being possible for one or two —$CH_2$— groups to be replaced by —O—, or $R^3$ and $R^4$ together can alternatively be —$(CH_2)_4$— or —$(CH_2)_5$— if they are bonded as substituents to a dioxolane system;

$A^1$, $A^2$ and $A^3$, independently of one another, are 1,4-phenylene, pyrazine-2,5-diyl, pyridazine-3,6-diyl, pyridine-2,5-diyl, pyrimidine-2,5-diyl, in which one or two hydrogen atoms can be replaced by F, trans-1,4-cyclohexylene, 1,3,4-thiadiazole-2,5-diyl, 1,3-dioxane-2,5-diyl, naphthalene-2,6-diyl;

$A^1$ can alternatively be a group of the formula

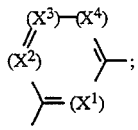

$M^1$, $M^2$ and $M^3$, independently of one another, are —O—, —CO—O—, —O—CO—, —$CH_2$—O—, —O—$CH_2$—, —$CH_2CH_2$— or —C≡C—;

$M^4$ is —$CH_2$—O—, —O—$CH_2$—, —CO—O—, —O—CO— or a single bond;

$X^1$, $X^2$, $X^3$ and $X^4$ are CH, CF or N, where the number of nitrogen atoms is 0, 1 or 2.

4. A compound as claimed in claim 2, the symbols and indices having the following meaning:

$R^1$ is a straight-chain or branched alkyl radical having 1 to 10 carbon atoms (with or without asymmetrical carbon atoms), it also being possible for one or two —$CH_2$— groups to be replaced by —O—, —CO—, —CO—O—, —O—CO—, —O—CO—O—, —CH=CH—, —CD≡C—, cyclopropanediyl or —Si$(CH_3)_2$—, and $R^2$ is a straight-chain or branched alkyl radical having 2 to 10 carbon atoms (with or without asymmetrical carbon atoms), wherein one or two —CH$_2$— groups are replaced by —O—, —CO—, —CO—O—, —O—CO—, —O—CO—O—, —CH=CH—, —C≡C—, cyclopropanediyl or —Si(CH$_3$)$_2$—; or $R^1$ and $R^2$, independently of one another, are one of the following chiral groups:

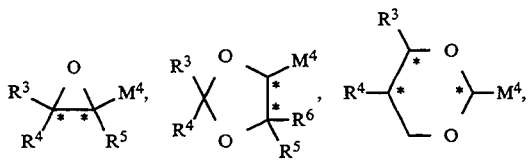

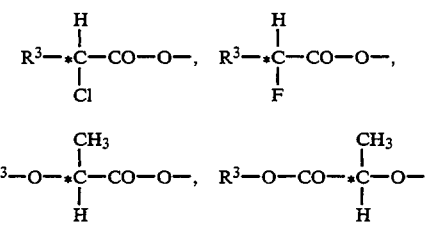

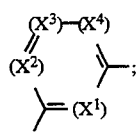

$R^3$, $R^4$, $R^5$ and $R^6$ independently of one another, are H or a Straight-chain or branched alkyl radical having 1 to 10 carbon atoms, it also being possible for one or two —CH$_2$— groups to be replaced by —O—, or $R^3$ and $R^4$ together can alternatively be —(CH$_2$)$_4$— or —(CH$_2$)$_5$— if they are bonded as substituents to a dioxolane system;

$A^1$, $A^2$ and $A^3$ independently of one another, are 1,4-phenylene, pyrazine-2,5-diyl, pyridine-2,5-diyl, pyrimidine-2,5-diyl, in which one or two hydrogen atoms can be replaced by F atoms, trans-1,4-cyclohexylene, 1,3,4-thiadiazole-2,5-diyl, naphthalene-2,6-diyl or 1,3-dioxane-2,5-diyl;

$A^1$ can alternatively be a group of the formula

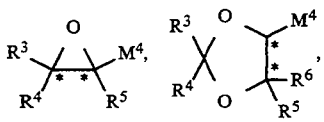

$M^1$, $M^2$ and $M^3$, independently of one another, are —O—, —CO—O—, —O—CO—, —CH$_2$—O—, —O—CH$_2$—, —CH$_2$CH$_2$— or —C≡C—;

$M^4$ is —CH$_2$—O—, —O—CH$_2$—, —CO—O—, —O—CO— or a single bond;

$X^1$, $X^2$, $X^3$ and $X^4$ are CH, CF or N, where the number of nitrogen atoms is 0, 1 or 2.

5. A compound as claimed in claim 2, the symbols and indices having the following meaning:

$R^1$ is a straight-chain or branched alkyl radical having 1 to 8 carbon atoms (with or without asymmetrical carbon atoms), it also being possible for one or two —CH$_2$— groups to be replaced by —O—, —CO—O—, —O—CO— or cyclopropanediyl;

$R^2$ is a straight-chain or branched alkyl radical having 2 to 8 carbon atoms (with or without asymmetrical carbon atoms), wherein one or two —CH$_2$— groups are replaced by —O—, —CO—O—, —O—CO— or cyclopropanediyl; or $R^1$ and $R^2$ independently of one another, are one of the following chiral groups:

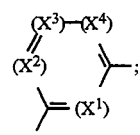

$R^3$, $R^4$, $R^5$ and $R^6$ independently of one another, are H or a straight-chain or branched alkyl radical having 1 to 8 carbon atoms;

$A^1$, $A^2$ and $A^3$ independently of one another, are 1,4-phenylene, pyridine-2,5-diyl, pyrimidine-2,5-diyl, in which one or two hydrogen atoms can be replaced by F atoms, or trans-1,4-cyclohexylene;

$A^1$ can alternatively be a group of the formula

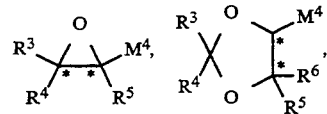

$M^1$, $M^2$ and $M^3$, independently of one another, are —O—, —CO—O—, —O—CO—, —O—CH$_2$—, —CH$_2$—O— or —CH$_2$CH$_2$—;

$M^4$ is —CH$_2$—O— or —CO—O—;

$X^1$, $X^2$, $X^3$ and $X^4$ are CH, CF or N, where the number of nitrogen atoms is 0, 1 or 2.

6. A liquid-crystal mixture as claimed in claim 1, comprising at least one compound of the formula (I) in which the symbols and indices have the following meanings:

$R^1$ and $R^2$, independently of one another, are a straight-chain or branched alkyl radical having 1 to 15 carbon atoms (with or without asymmetrical carbon atoms), it also being possible for one or two —CH$_2$—groups to be replaced by —O—, —CO—, —CO—O—, —O—CO—, —OCO—O—, —CH=CH—, —C≡C—, cyclopropanediyl or —Si(CH$_3$)$_2$—, or are one of the following chiral groups:

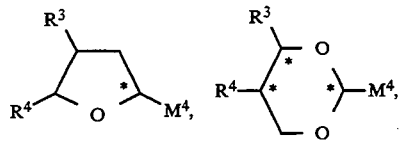

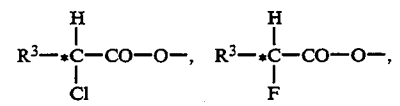

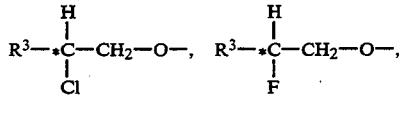

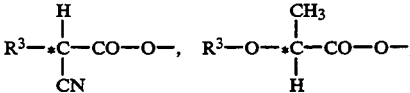

-continued

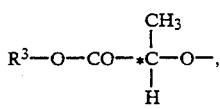

R³, R⁴, R⁵ and R⁶ independently of one another, are H or a straight-chain or branched alkyl radical having 1 to 15 carbon atoms, it also being possible for one or two —CH₂— groups to be replaced by —O—, or R³ and R⁴ together can alternatively be —(CH₂)₄— or —(CH₂)₅— if they are bonded as substituents to a dioxolane system;

A¹, A² and A³ independently of one another, are 1,4-phenylene, pyrazine-2,5-diyl, pyridazine-3,6-diyl, pyridine-2,5-diyl, pyrimidine-2,5-diyl, in which one or two hydrogen atoms can be replaced by F, trans-1,4-cyclohexylene, 1,3,4-thiadiazole-2,5-diyl, 1,3-dioxane-2,5-diyl or naphthalene-2,6-diyl;

A¹ can alternatively be a group of the formula

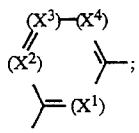

M¹, M² and M³, independently of one another, are —O—, —CO—, —CO—O—, —O—CO—, —CH₂—O—, —O—CH₂—, —CH₂CH₂— or —C≡C—;
M⁴ is —CH₂—O—, —O—CH₂—, —CO—O—, —O—CO— or a single bond;
X¹, X², X³ and X⁴ are CH, CF or N, where the number of nitrogen atoms is 0, 1 or 2; and
with the proviso that the group

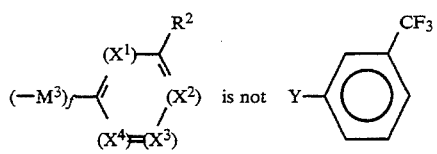

with Y being —CH₂—O—, —O—CH₂—, —COO— or —O—CO—.

7. A liquid-crystal mixture as claimed in claim 1, comprising at least one compound of the formula (I) in which the symbols and indices have the following meanings:

R¹ and R² independently of one another, are a straight-chain or branched alkyl radical having 1 to 10 carbon atoms (with or without asymmetrical carbon atoms), it also being possible for one or two —CH₂— groups to be replaced by —O—, —CO—, —CO—O—, —O—CO—, —CH=CH—, —C≡C—, cyclopropanediyl or —Si(CH₃)₂—, or are one of the following chiral groups:

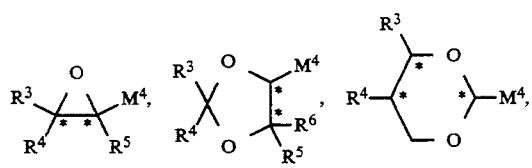

-continued $$R^3-*\overset{H}{\underset{Cl}{C}}-CO-O-, \quad R^3-*\overset{H}{\underset{F}{C}}-CO-O-,$$

$$R^3-O-*\overset{CH_3}{\underset{H}{C}}-CO-O-, \quad R^3-O-CO-*\overset{CH_3}{\underset{H}{C}}-O-,$$

$$R^3-*\overset{H}{\underset{CN}{C}}-CO-O-,$$

R³, R⁴, R⁵ and R⁶ independently of one another are H or a straight-chain or branched alkyl radical having 1 to 10 carbon atoms, it also being possible for one or two —CH₂— groups to be replaced by —O—, or R³ and R⁴ together can alternatively be —(CH₃)₄— or —(CH₂)₅— if they are bonded as substituents to a dioxolane system;

A¹, A² and A³ independently of one another, are 1,4-phenylene, pyrazine-2,5-diyl, pyridine-2,5-diyl, pyrimidine-2,5-diyl, in which one or two hydrogen atoms can be replaced by F atoms, trans-1,4-cyclohexylene, 1,3,4-thiadiazole-2,5-diyl, naphthalene-2,6-diyl or 1,3-dioxane-2,5-diyl;

A¹ can alternatively be a group of the formula

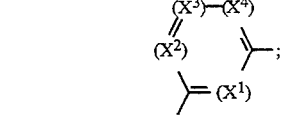

M¹, M² and M³ independently of one another, are —O—, —CO—O—, —O—CO—, —CH₂—O—, —O—CH₂—, —CH₂CH₂— or —C≡C—;
M⁴ is —CH₂—O—, —O—CH₂—, —CO—O—, —O—CO— or a single bond;
X¹, X², X³ and X⁴ are CH, CF or N, where the number of nitrogen atoms is 0, 1 or 2; and
with the proviso that the group with Y being —CH₂—O—, —O—CH₂—, —COO— or —O—CO—.

8. A liquid-crystal mixture as claimed in claim 1, comprising at least one compound of the formula (I) in which the symbols and indices have the following meanings:

R¹ and R² independently of one another, are an alkyl radical having 1 to 8 carbon atoms, it being possible for one or two —CH₂— groups to be replaced by —O—, —OCO— or cyclopropanediyl, or are the chiral groups:

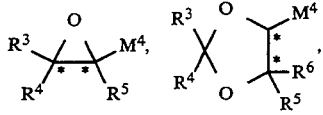

$R^3$, $R^4$, $R^5$ and $R^6$ independently of one another, are H or a straight-chain or branched alkyl radical having 1 to 8 carbon atoms;

$A^1$, $A^2$ and $A^3$ independently of one another, are 1,4-phenylene, pyridine-2,5-diyl, pyrimidine-2,5-diyl, in which one or two hydrogen atoms can be replaced by F atoms or trans-1,4cyclohexylene;

$A^1$ can alternatively be a group of the formula

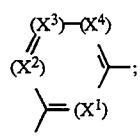

$M^1$, $M^2$ and $M^3$, independently of one another, are —O—, —CO—O—, —O—CO—, —O—CH$_2$—, —CH$_2$—O— or —CH$_2$CH$_2$—;

$M^4$ is —CH$_2$—O—, or —CO—O—;

$X^1$, $X^2$, $X^3$ and $X^4$ are CH, CF or N, where the number of nitrogen atoms is 0, 1 or 2; and with the proviso that the group

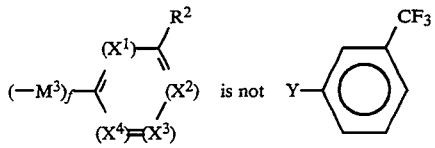

with Y being —CH$_2$—O—, —O—CH$_2$—, —COO— or —O—CO—.

9. A liquid-crystal mixture as claimed in claim 1, wherein the liquid-crystal mixture is ferroelectric.

10. A liquid-crystal mixture as claimed in claim 1, comprising from 0.01 to 60% by weight of at least one compound of the formula (I).

11. A switching and/or display device comprising outer plates, electrodes, at least one polarizer, at least one alignment layer and a liquid-crystalline medium, wherein the liquid-crystalline medium is a liquid-crystal mixture as claimed in claim 1.

* * * * *